(12) United States Patent
Davis

(10) Patent No.: US 9,977,007 B2
(45) Date of Patent: May 22, 2018

(54) BUBBLE SIZE DETERMINATION BASED ON BUBBLE STIFFNESS

(71) Applicant: CiDRA Corporate Services Inc., Wallingford, CT (US)

(72) Inventor: Michael A. Davis, Glastonbury, CT (US)

(73) Assignee: CIDRA CORPORATE SERVICES, INC., Wallingford, CT (US)

( * ) Notice: Subject to any disclaimer, the term of this patent is extended or adjusted under 35 U.S.C. 154(b) by 110 days.

(21) Appl. No.: 14/406,944

(22) PCT Filed: Jun. 13, 2013

(86) PCT No.: PCT/US2013/045568
§ 371 (c)(1),
(2) Date: Dec. 10, 2014

(87) PCT Pub. No.: WO2013/188620
PCT Pub. Date: Dec. 19, 2013

(65) Prior Publication Data
US 2015/0135801 A1    May 21, 2015

Related U.S. Application Data

(60) Provisional application No. 61/659,177, filed on Jun. 13, 2012.

(51) Int. Cl.
*G01N 3/40* (2006.01)
*G01N 33/38* (2006.01)
(Continued)

(52) U.S. Cl.
CPC ........... *G01N 33/383* (2013.01); *G01N 29/00* (2013.01); *G01N 29/024* (2013.01); *G01N 29/07* (2013.01);
(Continued)

(58) Field of Classification Search
CPC .................................................... G01N 33/383
See application file for complete search history.

(56) References Cited

U.S. PATENT DOCUMENTS

| 4,930,346 | A | * | 6/1990 | Paakkinen | ............... | G01N 3/24 |
| | | | | | | 73/54.31 |
| 4,959,994 | A | * | 10/1990 | Paakkinen | ........... | G01N 33/383 |
| | | | | | | 73/38 |

(Continued)

OTHER PUBLICATIONS

Influence of bubble size distribution on the echogenicity of ultrasound contrast agents: a study of SonoVue, Gorce JM Arditi, M, Schneider M., Invest Radiol. Jul. 2000; vol. 35, No. 11, pp. 661-671.

*Primary Examiner* — Ryan Walsh
(74) *Attorney, Agent, or Firm* — Ware, Fressola, Maguire & Barber LLP

(57) ABSTRACT

Apparatus is provided comprising a signal processing module configured with at least one processor and at least one memory including computer program code, the at least one memory and computer program code configured, with the at least one processor, to cause the apparatus at least to: receive signaling containing information about a stiffness of a concrete mixture; and determine an average bubble size of gas contained in the concrete mixture, based at least partly on the signaling received. The signal processing module may be configured to provide corresponding signaling containing information about the average bubble size of gas contained in the concrete mixture. The signal processing module may be configured to determine the pressure inside air bubbles and determine an average air bubble size of the gas contained in the concrete mixture, based at least partly on the pressure determined inside the air bubbles.

39 Claims, 3 Drawing Sheets

(51) Int. Cl.
*G01N 29/00* (2006.01)
*G01N 29/024* (2006.01)
*G01N 29/07* (2006.01)
*G01N 3/30* (2006.01)

(52) U.S. Cl.
CPC ....... *G01N 3/30* (2013.01); *G01N 2291/0232* (2013.01); *G01N 2291/02433* (2013.01); *G01N 2291/02827* (2013.01)

(56) References Cited

U.S. PATENT DOCUMENTS

| | | |
|---|---|---|
| 7,134,320 B2 | 11/2006 | Gysling et al. |
| 7,165,464 B2 | 1/2007 | Gysling et al. |
| 7,343,820 B2 | 3/2008 | Gysling et al. |
| 7,363,800 B2 | 4/2008 | Gysling et al. |
| 7,367,240 B2 | 5/2008 | Gysling et al. |
| 7,426,852 B1 | 9/2008 | Rothman |
| 2009/0205427 A1* | 8/2009 | Lootens ............... G01N 29/032 73/602 |

* cited by examiner

Apparatus, 10

Signal processing module 10a configured with at least one processor and at least one memory including computer program code, the at least one memory and computer program code configured, with the at least one processor, to cause the apparatus as least to:

receive signaling containing information about a stiffness of a concrete mixture; and determine an average bubble size of gas contained in the concrete mixture, based at least partly on the signaling received; and/or provide corresponding signaling containing information about the average bubble size of gas contained in the concrete mixture.

One or more other signal processing modules 10b, including memory modules (RAM, ROM, etc.); input/output (I/O) modules; and data, control and address busing, etc.

*FIG. 2a*

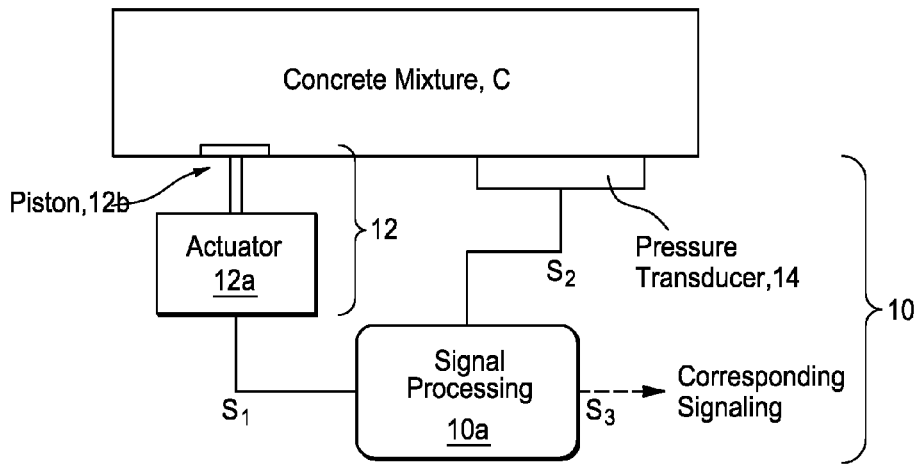

BUBBLE SIZE DETERMINATION BASED ON BUBBLE STIFFNESS

CROSS-REFERENCE TO RELATED APPLICATIONS

This application corresponds to international patent application serial no. PCT/US2013/045568, filed 13 Jun. 2013, which claims benefit to provisional patent application Ser. No. 61/659,177, filed 13 Jun. 2012 (WFVA/CiDRA file nos. 712-2.391), which is incorporated by reference in its entirety.

This application is related to PCT/US12/60822, filed 10 Oct. 2012 (WFVA/CiDRA file nos. 712-2.365-1/75), which claims benefit to provisional patent application Ser. No. 61/548,549, filed 18 Oct. 2011 (WFVA/CiDRA file nos. 712-2.365/75); and Ser. No. 61/548,563, filed 18 Oct. 2011 (WFVA/CiDRA file nos. 712-2.366/67), which are all incorporated by reference in their entirety.

This application is also related to U.S. patent application Ser. No. 13/637,065, filed 3 Dec. 2012 (WFVA/CiDRA file nos. 712-2.344-1-1/CCS-0039), which is a national stage application corresponding to PCT/US11/32697, claiming benefit to provisional application Ser. No. 61/342,586, filed 16 Apr. 2010, which are all incorporated in their entirety by reference, and assigned to the assignee of the present application.

This application is also related to U.S. patent application Ser. No. 13/583,062, filed 12 Sep. 2012 (WFVA/CiDRA file nos. 712-2.338-1/CCS-0033, 35, 40, and 45-49), which is a national stage application corresponding to PCT/US11/27731, claiming benefit to provisional patent application Ser. No. 61/311,993, filed 9 Mar. 2010 (WFVA/CiDRA file nos. 712-2.338/35); Ser. No. 61/312,023, filed 9 Mar. 2010 (WFVA/CiDRA file nos. 712-2.340/37), Ser. No. 61/342,585, filed 16 Apr. 2010 (WFVA/CiDRA file nos. 712-2.345/40-1), and Ser. No. 61/448,443, filed 2 Mar. 2011 (WFVA/CiDRA file nos. 712-2.353/47 and 51), which are all incorporated in their entirety by reference, and assigned to the assignee of the present application.

BACKGROUND OF THE INVENTION

1. Field of Invention

The present invention relates to a technique for bubble size determination in wet concrete; more particularly related to a technique for bubble size determination in wet concrete in order to control the amount of air in a mixture of concrete.

2. Description of Related Art

In the manufacturing process of many materials, gas is often required to achieve the optimum performance of the material. A primary example would be in the manufacture of concrete, where not only is a specific amount of air required in the product but also the bubble size of the gas component is critical. The assignee of the instant patent application has developed gas void fraction (GVF) measurement systems that perform well at determining the gas content however there are no readily available system for measurement of the bubble size.

In one implementation of a known GVF measurement system in concrete, the speed of sound of acoustic signals may be determined by injecting a signal into the concrete and measuring how long it takes for that acoustic signal to travel over a set distance. As shown in FIG. 1a, a piston may be used to cause a pressure fluctuation in the concrete and generate an acoustic signal. A pressure transducer arranged a set distance away is used to measure the arrival of the acoustic wave and then the speed of sound (SOS) in the concrete is determined. The GVF is then calculated using Wood's equation based on the SOS measurement.

One characteristic of bubbles is that the internal pressure is dependent on the bubble size, as shown by the Young-Laplace equation, which describes the difference between the inside and outside pressure of a bubble due to surface tension. As shown in FIG. 1b, as the bubble radius decreases the pressure and therefore the stiffness of the bubble increases (as referenced in "Influence of bubble size distribution on the echogenicity of ultrasound contrast agents: a study of SonoVue", Gorce J M, Arditi M, Schneider M., Invest Radiol. 2000 November; 35(11):661-71, which is hereby incorporated by reference in its entirety).

Known SONAR-Based GVF Meters

In the prior art, a number of techniques have been developed that rely on measuring the speed of sound through a material flowing through a pipe. These techniques include using a known SONAR-based GVF meter, density meter and potential mass fraction meter. In these techniques, a passive array-based sensor system is used to detect the presence and speed of acoustics traveling through the materials contained within a pipe. These materials can range from single phase homogeneous fluids to two or three phase mixtures of gases, liquids and solids. Since the measurements system is passive it relies on acoustics produced externally for the measurement. These acoustics can often times come from other equipment in or attached to the pipe such as pumps or valves.

Moreover, in these known techniques many times chemical additives may be added, including to a known flotation process in mineral processing to aid in the separation of the ore. The chemicals, known as frothers, control the efficiency of the flotation process by enhancing the properties of the air bubbles. An important parameter in flotation optimization is the gas volume fraction within a flotation cell. U.S. Pat. No. 7,426,852 B1, which is hereby incorporated by reference in its entirety, discloses approaches to make this measurement, and discloses a technique whereby the speed of sound in the aerated fluid is locally measured using a waveguide (pipe) in conjunction with a SONAR-based array. From the speed of sound measurement, the gas volume fraction can be calculated.

By way of example, see other techniques related to the use of such SONAR-based technology disclosed, e.g., in whole or in part in U.S. Pat. Nos. 7,165,464; 7,134,320; 7,363,800; 7,367,240; and 7,343,820, all of which are incorporated by reference in their entirety.

Moreover, air is a very important component of many materials, such as viscous liquids, slurries or solids, and mixtures of concrete. In particular, air is a critical ingredient when making concrete because it greatly improves the cured product damage resistance to freeze/thaw cycles. Chemical admixtures are typically added during mixing to create, entrain and stabilize billions of small air bubbles within the concrete. However, the entrained air in concrete has the disadvantage of reducing strength so there is always a trade-off to determine the right amount of air for a particular application. In order to optimize certain properties of concrete, it is important to control the entrained air present in the wet (pre-cured) concrete. Current methods for measuring the entrained air can sometimes be slow and cumbersome and additionally can be prone to errors. Moreover, the durability of concrete may be enhanced by entraining air in the fresh mix. This is typically accomplished through the addition of chemical admixes. The amount of admix is usually determined through empirical data by which a "recipe" is determined. Too little entrained air reduces the durability of the concrete and too much entrained air decreases the strength. Typically the nominal range of entrained air is about 5-8% by volume, and can be between 4% and 6% entrained air by volume in many applications. After being mixed in the mixer box, the concrete is then released to the truck. The level of entrained air is then measured upon delivery of the mix to the site. The draw back of the current method is that the mix is committed to the truck without verification of that the air level in the mix is within specification.

The aforementioned U.S. patent application Ser. No. 13/583,062 (WFVA/CiDRA file nos. 712-2.338-1/CCS-0033, 35, 40, and 45-49) discloses techniques for real time air measurement in wet concrete in concrete a rotary drum mixer, including implementing sensing technology in a hatch cover, as well as a stationary concrete mixer using an integrated sound source and two receivers, using SONAR-based technology developed and patented by the assignee of the instant patent application as well as that application.

SUMMARY OF THE INVENTION

The Basic Invention

In this application, a technique is set forth so that the bubble size can be determined in conjunction with the GVF.

One can use this phenomenon to deduce the mean or average bubble size using a system like that detailed in FIG. 1a, with some modifications. Essentially, a measurement of the stiffness of the concrete or concrete mixture will be substantially directly proportional to the mean bubble size. To determine the stiffness of the concrete or concrete mixture a simple combination of a force probe connected to an acoustic piston and a displacement sensor may be used to provide a stiffness factor. Alternate sensor configurations can also be used to determine the stiffness such as a combination of a drive current sent to the piston, acceleration of the piston's motion, and the force imparted into the concrete mixture.

An alternative method to determine the concrete stiffness is to check the displacement of the piston when an impulsive force is applied. A measure of the displacement, force and subsequent dampening of the piston's motion will lead to an understanding of the stiffness of the concrete mixture.

As described above, once the stiffness and GVF of the concrete is determined, the pressure inside the air bubbles can be calculated, which in turn will give a measurement of the mean bubble size.

Particular Embodiments

The present application provides new techniques or ways of real time measurement of entrained air in wet concrete, consistent with, and further building on that set forth in, the aforementioned PCT/US12/60822, filed 10 Oct. 2012 (WFVA/CiDRA file nos. 712-2.365-1/CCS-0075), as well as U.S. patent application Ser. No. 13/583,062, filed 12 Sep. 2012 (WFVA/CiDRA file nos. 712-2.338-1/CCS-0033, 35, 40, and 45-49).

By way of example, the present invention provides new measurement devices that may include, or take the form of, apparatus featuring: a signal processing module configured with at least one processor and at least one memory including computer program code, the at least one memory and computer program code configured, with the at least one processor, to cause the apparatus at least to:
receive signaling containing information about a stiffness of concrete or a concrete mixture; and
determine an average bubble size of gas contained in the concrete or concrete mixture, based at least partly on the signaling received.

According too some embodiments, the present invention may include one or more of the following features:

The signal processing module may be configured to provide corresponding signaling containing information about the average bubble size of gas contained in the concrete mixture.

The signal processing module may be configured to determine the pressure inside air bubbles and determine an average air bubble size of the gas contained in the concrete mixture, based at least partly on the pressure determined inside the air bubbles.

According to some embodiments of the present invention, the apparatus may include a combination of a force probe connected to an acoustic piston and a displacement sensor that is configured to provide associated signaling containing information about the stiffness of the concrete mixture. The signal processing module may be configured to receive the associated signaling containing information about a force applied by the acoustic piston to the concrete mixture and sensed by the force probe, and information about a displacement of the acoustic piston in relation to the concrete mixture sensed by the displacement sensor, and configured to determine the stiffness factor of the concrete mixture, based at least partly the associated signaling received.

According to some embodiments of the present invention, the apparatus may include a combination configured with a piston to impart a force into the concrete mixture, a drive current sensor to sense a drive current sent to the piston, and a piston accelerometer to sense an acceleration of the piston's motion, and also configured to provide associated signaling containing information about the stiffness of the concrete mixture. The signal processing module may be configured to receive the associated signaling containing information about the drive current sent to the piston and sensed by the drive current sensor, about the acceleration of the piston's motion sensed by the piston accelerometer, and configured to determine the stiffness of the concrete mixture based at least partly on the associated signaling received.

According to some embodiments of the present invention, the apparatus may include a combination configured with a piston to apply an impulsive force to the concrete mixture and at least one sensor to sense or determine a displacement of the piston when the impulsive force is applied to the concrete mixture, the impulsive force applied to the concrete mixture and subsequent dampening of the piston's motion, and also configured to provide associated signaling containing information about the stiffness of the concrete mixture. The signal processing module may be configured to receive the associated signaling information about the displacement of the piston when the impulsive force is applied to the concrete mixture, the impulsive force applied to the concrete mixture, and subsequent dampening of the piston's motion, and configured to determine the stiffness of the concrete mixture based at least partly on the associated signaling received.

According to some embodiments of the present invention, the signal processing module may be configured to determine the average bubble size of the gas contained in the concrete mixture, based at least partly on a measurement of the stiffness of the concrete mixture being substantially directly proportional to the average bubble size.

According to some embodiments of the present invention, the apparatus may include a pressure transducer configured to sense at least one acoustic signal injected into the concrete mixture and provide associated signaling containing information about the information about the at least one acoustic signal sensed. The signal processing module may be configured to receive the associated signaling and to determine a gas volume fraction (GVF) of the concrete mixture, based at least partly on the associated signaling received.

According to some embodiments of the present invention, the signal processing module may be configured to receive in the signaling information about at least one acoustic signal injected into the concrete mixture, and to determine a gas volume fraction (GVF) of the concrete mixture, based at least partly on the signaling received. The signal processing module may be configured to determine the GVF of the concrete mixture, based at least partly on determining the speed of sound of the at least one acoustic signal injected in the concrete mixture, including by injecting the at least one acoustic signal into the concrete mixture and measuring how long the at least one acoustic signal takes to travel over a set distance. The apparatus may include a combination having a piston and an actuator configured to cause a pressure fluctuation in the concrete mixture and generate the at least one acoustic signal; a pressure transducer configured the set distance away from the piston, configured to sense the at least one acoustic signal, and to provide associated signaling containing information about the arrival of the at least one acoustic wave; and the signal processing module being configured to receive the associated signaling and to determine a speed of sound (SOS) in the concrete mixture and the GVF of the concrete mixture, including by using a Wood's equation based on a SOS measurement.

The stiffness of the concrete mixture may be based on, or may be understood to include, or may take the form of, or may be understood to be, the rigidity of the concrete mixture as an object, including the extent to which the concrete mixture resists deformation in response to an applied force.

Methods

According to some embodiments of the present invention, the present invention may take the form of a method that may include, or take the form of, steps for receiving in a signal processor module signaling containing information about the stiffness and a gas volume fraction (GVF) of a concrete mixture; and determining in the signal processor module an average bubble size of gas contained in the concrete mixture, based at least partly on the signaling received.

This method may also include some combination of the aforementioned features set forth herein.

The present invention makes important contributions to this current state of the art for bubble size determination in wet concrete, as well as techniques to control the amount of air in a mixture of concrete.

BRIEF DESCRIPTION OF THE DRAWING

The drawing includes FIGS. 1-2d, which are not necessarily drawn to scale, as follows:

FIG. 2a shows a diagram of apparatus, e.g., including a signal processing module, according to some embodiments of the present invention.

FIG. 2b shows a diagram of apparatus, e.g., including a combination of a signal processing module, an actuator, a piston and a transducer, according to some embodiments of the present invention.

DETAILED DESCRIPTION OF BEST MODE OF THE INVENTION

FIGS. 2a, 2b

Figure 1A:
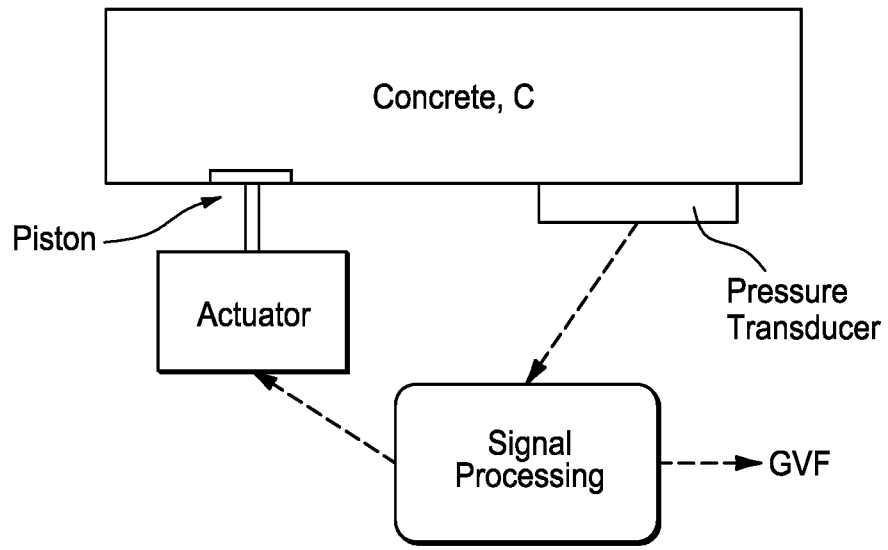
FIG. 1a is a diagram of an arrangement known in the art for determining the entrained air in concrete or a concrete mixture, including a SONAR-based arrangement using a SOS measurement
Figure 1B:
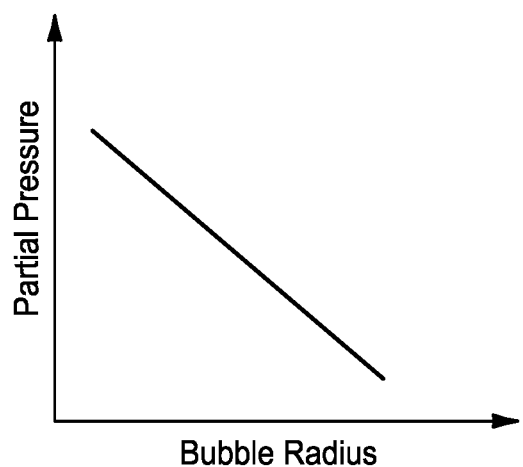
FIG. 1b is a graph of partial pressure versus bubble radius consistent with that known in the art.

FIGS. 2a and 2b show, by way of example, the present invention that may include, or take the form of, apparatus 10 featuring: a signal processing module 10a configured with at least one processor or signal processor and at least one memory including computer program code, the at least one memory and computer program code configured, with the at least one processor or signal processor, to cause the apparatus at least to:
  receive signaling containing information about a stiffness of concrete or a concrete mixture C; and
  determine an average bubble size of gas contained in the concrete or concrete mixture C, based at least partly on the signaling received.

In FIG. 2a, the signaling may including first signaling $S_1$, e.g., provided by a combination 12 having an actuator 12a and a piston 12b, and may also include second signaling $S_2$, e.g., provided by a pressure transducer 14, consistent with that shown in FIG. 2b.

The signal processing module 10a may be configured to provide corresponding signaling $S_3$, e.g., containing information about the average bubble size of gas contained in the concrete or concrete mixture C. By way of example, the corresponding signaling $S_3$ may be further processed, e.g., to display the average bubble size in the concrete or concrete mixture C, or to control the manufacturing process of the concrete or concrete mixture C, such as by dosing the concrete mixture with some agent to adjust the average bubble size in the concrete or concrete mixture.

By way of example, the signal processing module 10a may be configured to determine the pressure inside air bubbles and determine an average air bubble size of the gas contained in the concrete or concrete mixture C, based at least partly on the pressure determined inside the air bubbles. This determination process may be used in relation to other types of kinds of gases other than air.

Figure 2C:
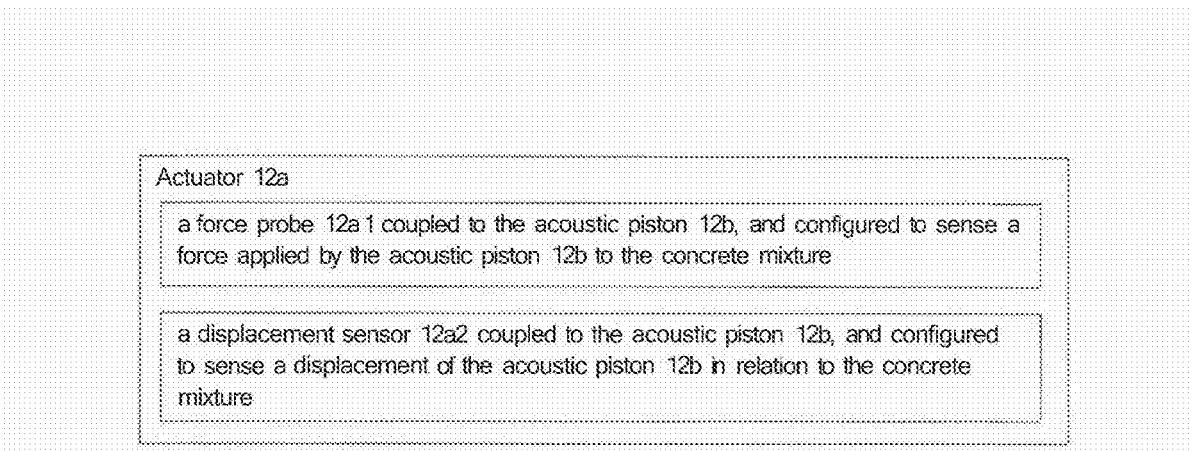
FIG. 2c shows an actuator, according to some embodiments of the present invention.

According to some embodiments of the present invention, and consistent with that shown in FIG. 2c, the apparatus 10 may include a force probe 12a1 connected or coupled to the acoustic piston 12b and a displacement sensor 12a2 that is configured to provide associated signaling containing information about the stiffness of the concrete mixture. By way of example, the force probe 12a1 and displacement sensor 12a2 may forms part of the actuator 12a, or alternatively be separate stand alone elements, all within the spirit of the present invention. The signal processing module 10a may be configured to receive the associated signaling containing information about a force applied, e.g., by the acoustic piston 12b to the concrete or concrete mixture C and sensed by the force probe 12a1, and information about a displacement of the acoustic piston 12b in relation to the concrete or concrete mixture C sensed by the displacement sensor 12a2, and to determine the stiffness factor of the concrete or concrete mixture C, based at least partly the associated signaling received.

Figure 2D:
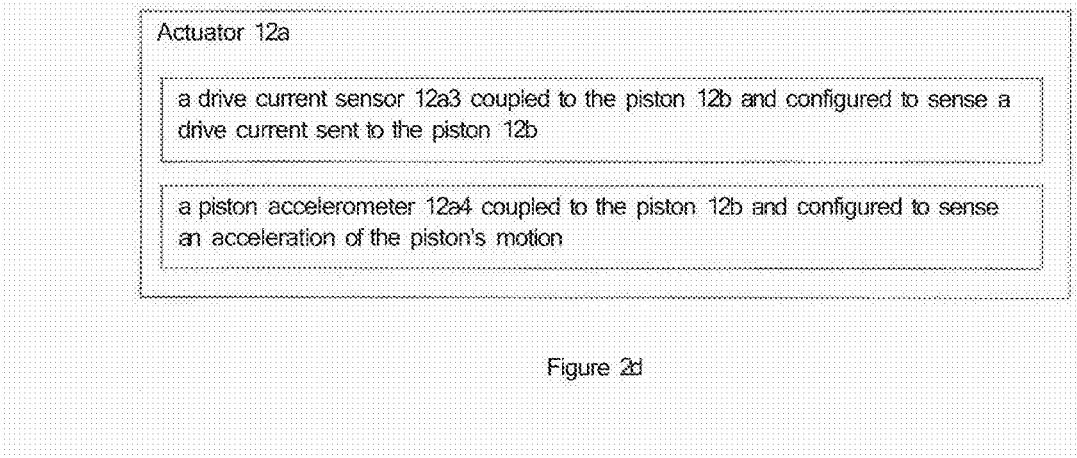
FIG. 2d shows an actuator, according to some embodiments of the present invention.

According to some embodiments of the present invention, and consistent with that shown in FIG. 2d, the apparatus 10 may include a combination, e.g., configured with a piston like element 12b to impart a force into the concrete or concrete mixture C, a drive current sensor 12a3 to sense a drive current sent to the piston 12b, and a piston accelerometer 12a4 to sense an acceleration of the piston's motion, and also configured to provide associated signaling containing information about the stiffness of the concrete mixture. The signal processing module may be configured to receive the associated signaling containing information about the drive current sent to the piston 12b and sensed by the drive current sensor, about the acceleration of the piston's motion sensed by the piston accelerometer, and to determine the stiffness of the concrete mixture based at least partly on the associated signaling received. By way of example, the drive current sensor and the piston accelerometer may form part of the actuator 12a, or alternatively be separate stand alone elements, all within the spirit of the present invention.

According to some embodiments of the present invention, the apparatus 10 may include a combination, e.g., configured with a piston like element 12b to apply an impulsive force to the concrete or concrete mixture C and at least one sensor to sense or determine a displacement of the piston 12b when the impulsive force is applied to the concrete or concrete mixture C, the impulsive force applied to the concrete or concrete mixture C and subsequent dampening of the piston's motion. Such a combination may also be configured to provide associated signaling containing information about the stiffness of the concrete or concrete mixture C. By way of example, the at least one sensor may form part of the actuator 12a, or alternatively be a separate stand alone element, all within the spirit of the present invention. The signal processing module 10a may be configured to receive the associated signaling information about the displacement of the piston when the impulsive force is applied to the concrete mixture, the impulsive force applied to the concrete mixture, and subsequent dampening of the piston's motion, and to determine the stiffness of the concrete or concrete mixture C based at least partly on the associated signaling received.

The signal processing module 10a may be configured to determine the average bubble size of the gas contained in the concrete mixture C, based at least partly on a measurement of the stiffness of the concrete or concrete mixture C being substantially directly proportional to the average bubble size.

According to some embodiments of the present invention, the apparatus 10 may include the pressure transducer 14 configured to sense at least one acoustic signal injected into the concrete mixture and provide associated signaling containing information about the at least one acoustic signal sensed. The signal processing module 10a may be configured to receive the associated signaling and to determine a gas volume fraction (GVF) of the concrete or concrete mixture C, based at least partly on the associated signaling received.

According to some embodiments of the present invention, the signal processing module 10a may be configured to receive in the signaling information about at least one acoustic signal injected into the concrete or concrete mixture, and to determine a gas volume fraction (GVF) of the concrete mixture, based at least partly on the signaling received. By way of example, the signal processing module 10a may be configured to determine the GVF of the concrete or concrete mixture C, based at least partly on determining the speed of sound of the at least one acoustic signal injected in the concrete or concrete mixture C, including by injecting the at least one acoustic signal into the concrete or concrete mixture C and measuring how long the at least one acoustic signal takes to travel over a set distance. The apparatus 10 may include a combination 12 having the actuator 12a and the piston 12b configured to cause a pressure fluctuation in the concrete or concrete mixture C and generate the at least one acoustic signal; the pressure transducer 14 configured the set distance away from the piston 12b configured to sense the at least one acoustic signal, and to provide associated signaling containing information about the arrival of the at least one acoustic wave. The signal processing module 10a may be configured to receive the associated signaling and to determine the SOS in the concrete or concrete mixture C and the GVF of the concrete or concrete mixture C, including by using a Wood's equation based on a SOS measurement.

Signal Processing or Signal Processing Module 10a

By way of example, and consistent with that described herein, the functionality of the signal processing or signal processing module 10a may be implemented using hardware, software, firmware, or a combination thereof, although the scope of the invention is not intended to be limited to any particular embodiment thereof. In a typical software implementation, the signal processor would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality set forth in the signal processing block 10a, such as determining the gas volume fraction of the aerated fluid based at least partly on the speed of sound measurement of the acoustic signal that travels through the aerated fluid in the container, as well as other functionality described herein without undue experimentation. The scope of the invention is not intended to be limited to any particular implementation using technology now known or later developed in the future. Moreover, the scope of the invention is intended to include the signal processor being a stand alone module, as shown, or in the combination with other circuitry for implementing another module.

It is also understood that the apparatus 10 may include one or more other modules, components, circuits, or circuitry 10b for implementing other functionality associated with the apparatus that does not form part of the underlying invention, and thus is not described in detail herein. By way of example, the one or more other modules, components, circuits, or circuitry 10b may include random access memory, read only memory, input/output circuitry and data and address buses for use in relation to implementing the signal processing functionality of the signal processor 10a, or devices or components related to mixing or pouring concrete in a ready-mix concrete truck or adding chemical additives, etc.

The Dual Frequency Techniques for Determining Entrained Air

The scope of the invention may include, by way of example, using dual frequency techniques to determine the entrained air in the concrete or concrete mixture C, according to some embodiments of the present invention. For example, a signal processor 10a may be configured to receive signaling containing information about an acoustic signal injected into a mixture of concrete; and determine a measurement of air percentage in the mixture of concrete based at least partly on a dual frequency technique that depends on a relationship between the acoustic signal injected and the signaling received.

Phase Sensitive Dual Frequency Lock-In Measurement for Concrete Air Content with Quality Factor The scope of the invention may include using other techniques to determine the entrained air in the concrete or concrete mixture C, according to some embodiments of the present invention. By way of example, another approach for the measurement of air percentage in concrete, e.g., is to measure the speed of sound (SOS) in the mixture and then through the use of the Wood's equation to calculate the amount of gas present. Various acoustic speed of sound measurements used in relation to SONAR-based technology as well as other sound receiving technology are set forth below with numerous patents disclosing this technology. This measurement of air percentage in concrete can be very difficult in materials like concrete where acoustic waves will quickly die out in strength due to the material's constituents along with other factors. This can be overcome by injecting a strong acoustic signal into the mixture at one point and then timing the signal propagation through a representative section of the material. However, this approach requires significant amounts of energy to produce a large compression wave in the concrete.

According to some embodiments of the present invention, a variation of this approach may be implemented that would require a modest acoustic signal to be injected but a very sensitive detection technique that can pull the injected signal out of the other acoustic "noise" that is present in the system. One detection technique that is well suited for this is a phase sensitive lock-in approach.

In a lock-in approach, a reference signal may be injected into the mixture and that same signal may be mixed with a resultant detected signal from the mixture. After a low pass filter is used to get the DC component of the result, a value may be obtained that is proportional to the amplitude and phase of the detected signal at the reference frequency. If the same calculation is made with the reference shifted by 90 deg, the phase and amplitude components can be separately determined. If one takes θref as the reference phase, θdet as the detected phase, Adet as the detected signal amplitude at the frequency of interest, then the signal amplitude and the signal phase difference may be determined using the following set of equations:

$\theta = \theta det - \theta ref$, $X \sim A det \cos(\theta)$, $Y \sim A det \cos(\theta+90 \deg) = A det \sin(\theta)$, Signal amplitude $= A det = (X^2 * Y^2)^{1/2}$, and Signal phase difference $= \theta = \tan^{-1}(Y/X)$.

The signal phase difference calculated along with the frequency can then be used to determine the time of propagation of the signal in the material and then the SOS.

Ambiguity in the Detected Acoustic Signal

However, an ambiguity exists once the detected signal has gone though a propagation time equal to 2*pi of the injected signal (or any multiple). This can be somewhat prevented by assuring that the frequency used for injection is low enough that the time delay can not introduce the ambiguity, however this will severely restrict the operational range of the measurement. Variations in the air content along with the attenuation characteristic of the materials may force the system to operate in a region where the ambiguity will exist. This can be prevented by injecting two slightly different frequencies into the material and then detecting each to determine the relative phase between the two injected signals, e.g., using the acoustic probe that include two dynamic transducers. An ambiguity can still exist but it will be a function of the difference of the two injected signals rather than just the single injected frequency.

An additional issue with a system such as this which calculates a SOS is the reliability of the calculation. The lock-in scheme above will always give a number for the phase delay and therefore the SOS but an indication or quality factor is needed to be able to gauge the reliability of that calculation. Since from the phase calculation the amplitude of the signal may also be obtained, this can be used for calculation of a quality metric. If one takes the amplitude of the signal at the injected frequency and compares that to several amplitudes of signals around that frequency, then one can get an indication of how the signal of interest is, or relates, to the surrounding "noise". If one takes the amplitude of the signal of interest at Asig and also take a sample of four other signals spaced adjacent to the original of A0, A1, A2 and A3, then one can average the four comparison signals and consider this the adjacent noise Anoise=(A0+A1+A2+A3)/4. A difference over sum normalization will give one a quality signal, Q, that varies between −1 to 1. With 1 representing a good quality, a 0 indicating same signal strength at frequency of interest as other frequencies and a −1 as a very weak signal of interest.

$Q = (A\text{sig} - A\text{noise})/(A\text{sig} + A\text{noise})$.

Examples of Known SONAR-Based Technology

Techniques are known for impact and coherent noise sources for acoustic speed of sound measurements, including such acoustic speed of sound measurements used in relation to SONAR-based technology as well as other sound receiving technology as shown and described herein. By way of example, the SONAR-based entrained air meter may take the form of SONAR-based meter and metering technology disclosed, e.g., in whole or in part, in U.S. Pat. Nos. 7,165,464; 7,134,320; 7,363,800; 7,367,240; and 7,343,820, all of which are incorporated by reference in their entirety.

A. Introduction

The known SONAR-based technology includes a gas volume fraction meter (known in the industry as a GVF-100 meter) that directly measures the low-frequency sonic speed (SOS) of the liquid or slurry flowing through a pipe. By way of example, the SONAR-based entrained air meter may take the form of SONAR-based meter and metering technology disclosed, e.g., in whole or in part, in U.S. Pat. Nos. 7,165,464; 7,134,320; 7,363,800; 7,367,240; and 7,343,820, all of which are incorporated by reference in their entirety. Using the Wood's equation, the volume percent of any gas bubbles or the gas void fraction (GVF) is determined from the measured SOS. The Wood's equation requires several other inputs in addition to the measured SOS of liquid/gas mixture. One of the additional inputs in particular, the static pressure of the liquid/gas mixture, can be very important for an accurate calculation of the GVF. To a first order, if the static pressure used for the GVF calculation differs from the actual static pressure of the liquid/gas mixture, then the calculated GVF may typically differ from the actual GVF by 1% as well. For example:

Static Pressure used for GVF calculation=20 psia
Calculated GVF=2%
Actual Static Pressure=22 psia
Static pressure error=22/20−1=0.1=10%
Actual GVF=2%×(1+0.1)=2.2% (10% error)

In many cases, the static pressure of the liquid/gas mixture is available through existing process plant instrumentation. In this case, the measured static pressure can be input directly to the GVF calculation through, e.g., an analog 4-20 mA input in the SONAR-based gas volume fraction transmitter (e.g. GVF-100 meter). Alternatively, a correction to the calculated GVF can be made in the customer DCS for any variation from the fixed pressure that was used to originally calculate the GVF.

In other cases, a static pressure transmitter can be added to the process plant specifically to measure the static pressure used for the GVF calculation. The measured pressure can either be input to the SONAR-based gas volume fraction transmitter (e.g., GVF-1200) or correction made in the DCS as described above.

Occasionally, a the SONAR-based gas volume fraction meter (e.g., GVF-100) may be installed at a location in the process that does not already have a static pressure gauge installed and it is impractical to add one. This could be a location where there is no existing penetration of the pipe to sense the pressure and it would be difficult or expensive to add one. In the case, where a traditional pressure gauge is not available and it is desirable to have a static pressure measurement the following description of a non-intrusive (clamp on) static pressure measurement could be used.

B. Description

For example, according to some embodiments of the present invention, a non-intrusive static pressure measurement may be sensed using traditional strain gauges integrated into the sensor band of the SONAR-based gas volume fraction sensing technology (e.g. the known GVF-100 meter). As the static pressure inside the pipe changes, the static strain on the outside of the pipe also changes. Using a thin-wall assumption for simplicity (t/R<10, where t is the wall thickness and R is the radius) the tangential strain due to internal static pressure is:

$$\varepsilon = \frac{pR}{Et},$$

where $\varepsilon$ is the tangential strain (inch/inch), R is the radius (inch), E is the modulus of elasticity (lb/in2) and t is the wall thickness (inch). The radius, wall thickness and modulus is generally known, or at least constant and so if the tangential strain is measured the internal static pressure can be determined.

By way of example, according to one embodiment of the present invention, four strain gauges could be arranged on the sensor band of the SONAR-based gas volume fraction sensing technology (e.g. the known GVF-100 meter) in a Wheatstone bridge configuration to maximize strain sensitivity and minimize temperature effects. In this case, the sensitivity assuming a strain gauge factor of 2, the sensitivity is approximately 13 µV/µE, where V is volts. Assuming a 4-inch schedule 40 carbon steel pipe, a one psi change in pressure would cause a 4 µV change in Wheatstone bridge output. This sensitivity would increase for larger diameter pipes which generally have a smaller t/R.

The integrated pressure gauge could be calibrated in-situ for best accuracy, but it may be sufficient to normalize the pressure output to a certain know state then use the tangential strain formula above with know pipe parameters to calculate the pressure from the measured strain.

The SONAR-based entrained air meter and metering technology are known in the art and may take the form of a SONAR-based meter disclosed, e.g., in whole or in part in U.S. Pat. Nos. 7,165,464; 7,134,320; 7,363,800; 7,367,240; and 7,343,820, all of which are incorporated by reference in their entirety. The SONAR-based entrained air meter and metering technology is capable of providing a variety of information, including the pure phase density and pure phase liquid sound speed is known, such that the GVF can be determined by measuring the speed of sound and then applying the Woods Equation.

Determining the GVF by measuring the speed of sound can provide fast an accurate data. Also the SOS measurement system can be very flexible and can easily be configured to work with different concrete containers and sample particular volumes.

Consistent with that described above, the SONAR-based entrained air meter and metering technology are known in the art and may take the form of a SONAR-based meter disclosed, e.g., in whole or in part in U.S. Pat. Nos. 7,165,464; 7,134,320; 7,363,800; 7,367,240; and 7,343,820.

Other Known Technology

The pistons, acoustic transmitters, actuators, the acoustic receiver or receiver probes, pressure transducers, and/or transponders are devices that are known in the art, and the scope of the invention is not intended to be limited to any particular type or kind either now known or later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
   a sensor combination configured to: sense a force imparted on a concrete mixture and a response to the force imparted, and provide signaling containing information about a stiffness of the concrete mixture based upon the force and the response to the forced imparted; and
   at least one signal processor and at least one memory including computer program code configured to cause the apparatus at least to:
   receive signaling, and determine corresponding signaling containing information about an average bubble size of gas contained in the concrete mixture, based at least partly on the signaling received.

2. Apparatus according to claim 1, wherein the at least one signal processor is configured to provide the corresponding signaling containing information about the average bubble size of gas contained in the concrete mixture.

3. Apparatus according to claim 1, wherein the at least one signal processor is configured to determine the pressure inside air bubbles and determine an average air bubble size of the gas contained in the concrete mixture, based at least partly on the pressure determined inside the air bubbles.

4. Apparatus according to claim 1, wherein the sensor combination comprises: an actuator and an acoustic piston, the actuator having a combination of a force probe connected to the acoustic piston and a displacement sensor, the actuator configured to provide associated signaling containing information about a force applied by the acoustic piston to the concrete mixture and sensed by the force probe, and information about a displacement of the acoustic piston in relation to the concrete mixture sensed by the displacement sensor.

5. Apparatus according to claim 4, wherein the at least one signal processor is configured to receive the associated signaling, and to determine a stiffness factor of the concrete mixture, based at least partly the associated signaling received.

6. Apparatus according to claim 1, wherein the sensor combination comprises: a combination having an actuator and a piston, the piston configured to impart a force into the concrete mixture, the actuator having a drive current sensor configured to sense a drive current sent to the piston, and having a piston accelerometer configured to sense an acceleration of the piston's motion, and the actuator also configured to provide associated signaling containing information about the drive current sent to the piston and sensed by the drive current sensor, and about the acceleration of the piston's motion sensed by the piston accelerometer.

7. Apparatus according to claim 6, wherein the at least one signal processor is configured to receive the associated signaling, and to determine the stiffness of the concrete mixture based at least partly on the associated signaling received.

8. Apparatus according to claim 1, wherein the sensor combination comprises: a combination having an actuator and a piston, the piston configured to apply an impulsive force to the concrete mixture, and the actuator having at least one sensor to sense or determine a displacement of the piston when the impulsive force is applied to the concrete mixture, the impulsive force applied to the concrete mixture and subsequent dampening of the piston's motion, and the actuator also configured to provide associated signaling containing information about the displacement of the piston when the impulsive force is applied to the concrete mixture, the impulsive force applied to the concrete mixture, and subsequent dampening of the piston's motion.

9. Apparatus according to claim 8, wherein the at least one signal processor is configured to receive the associated signaling, and to determine the stiffness of the concrete mixture based at least partly on the associated signaling received.

10. Apparatus according to claim 1, wherein the at least one signal processor is configured to determine the average bubble size of the gas contained in the concrete mixture, based at least partly on a measurement of the stiffness of the concrete mixture being substantially directly proportional to the average bubble size.

11. Apparatus according to claim 1, wherein the sensor combination comprises: a pressure transducer configured to sense at least one acoustic signal injected into the concrete mixture and provide associated signaling containing information about the at least one acoustic signal sensed.

12. Apparatus according to claim 11, wherein the at least one signal processor is configured to receive the associated signaling and to determine a gas volume fraction (GVF) of the concrete mixture, based at least partly on the associated signaling received.

13. Apparatus according to claim 1, wherein the at least one signal processor is configured to receive in the signaling information about at least one acoustic signal injected into the concrete mixture, and to determine a gas volume fraction (GVF) of the concrete mixture, based at least partly on the signaling received.

14. Apparatus according to claim 13, wherein the at least one signal processor is configured to determine the GVF of the concrete mixture, based at least partly on determining the speed of sound of the at least one acoustic signal injected in the concrete mixture, including where the at least one acoustic signal is injected into the concrete mixture and measuring how long the at least one acoustic signal takes to travel over a set distance.

15. Apparatus according to claim 14, wherein the sensor combination comprises:
  a combination having a piston and an actuator configured to cause a pressure fluctuation in the concrete mixture and generate the at least one acoustic signal;
  a pressure transducer configured the set distance away from the piston, configured to sense the at least one acoustic signal, and configured to provide associated signaling containing information about the arrival of the at least one acoustic wave; and
  the at least one signal processor being configured to receive the associated signaling and to determine a speed of sound (SOS) in the concrete mixture and the GVF of the concrete mixture, including by using a Wood's equation based on a SOS measurement.

16. Apparatus according to claim 1, wherein the stiffness of the concrete mixture is, includes, or takes the form of, the rigidity of the concrete mixture as an object, including the extent to which the concrete mixture resists deformation in response to an applied force.

17. A method comprising:
  sensing, with a sensor combination, a force imparted on a concrete mixture and a response to the force imparted;
  providing, with the sensor combination, signaling containing information about a stiffness and a gas volume fraction (GVF) of the concrete mixture based upon the force and the response to the forced imparted;
  receiving, in a signal processor, the signaling; and
  determining, in the signal processor, corresponding signaling containing information about an average bubble size of gas contained in the concrete mixture, based at least partly on the signaling received.

18. A method according to claim 17, wherein the method comprises: providing with the signal processor the corresponding signaling containing information about the average bubble size of gas contained in the concrete mixture.

19. A method according to claim 17, wherein the method comprises: determining with the signal processor the pressure inside air bubbles and determine an average air bubble size of the gas contained in the concrete mixture, based at least partly on the pressure determined inside the air bubbles.

20. A method according to claim 17, wherein the method comprises: configuring the sensor combination with a force probe connected to an acoustic piston and a displacement sensor to provide associated signaling containing information about the force applied by the acoustic piston to the concrete mixture and sensed by the force probe, and information about a displacement of the acoustic piston in relation to the concrete mixture sensed by the displacement sensor.

21. A method according to claim 20, wherein the method comprises: configuring the signal processor to receive the associated signaling, and to determine a stiffness factor of the concrete mixture, based at least partly the associated signaling received.

22. A method according to claim 17, wherein the method comprises: configuring the sensor combination with a piston to impart the force into the concrete mixture, a drive current sensor to sense a drive current sent to the piston, and a piston accelerometer to sense an acceleration of the piston's motion, and also configured to provide associated signaling containing information about the drive current sent to the piston and sensed by the drive current sensor, and about the acceleration of the piston's motion sensed by the piston accelerometer.

23. A method according to claim 22, wherein the method comprises configuring the signal processor to receive the associated signaling, and to determine the stiffness of the concrete mixture based at least partly on the associated signaling received.

24. A method according to claim 17, wherein the method comprises: configuring the sensor combination with a piston to apply an impulsive force to the concrete mixture and at least one sensor to sense or determine a displacement of the piston when the impulsive force is applied to the concrete mixture, the impulsive force applied to the concrete mixture and subsequent dampening of the piston's motion, and also configured to provide associated signaling containing information about the displacement of the piston when the impulsive force is applied to the concrete mixture, the impulsive force applied to the concrete mixture, and subsequent dampening of the piston's motion.

25. A method according to claim 24, wherein the method comprises: configuring the signal processor to receive the associated signaling, and to determine the stiffness of the concrete mixture based at least partly on the associated signaling received.

26. A method according to claim 17, wherein the method comprises: determining with the signal processor the average bubble size of the gas contained in the concrete mixture, based at least partly on a measurement of the stiffness of the concrete mixture being substantially directly proportional to the average bubble size.

27. A method according to claim 17, wherein the method comprises: configuring the sensor combination with a pressure transducer to sense at least one acoustic signal injected into the concrete mixture and provide associated signaling containing information about the at least one acoustic signal sensed.

28. A method according to claim 27, wherein the method comprises: receiving with the signal processor the associated signaling and determining with the signal processor a gas volume fraction (GVF) of the concrete mixture, based at least partly on the associated signaling received.

29. A method according to claim 17, wherein the method comprises: receiving, with the signal processor, the signaling containing information about at least one acoustic signal injected into the concrete mixture; and determining, with the signal processor, a gas volume fraction (GVF) of the concrete mixture, based at least partly on the signaling received.

30. A method according to claim 29, wherein the method comprises: determining, with the signal processor, the GVF of the concrete mixture, based at least partly on determining the speed of sound of the at least one acoustic signal injected in the concrete mixture, including where the at least one acoustic signal is injected into the concrete mixture and measuring how long the at least one acoustic signal takes to travel over a set distance.

31. A method according to claim 30, wherein the method comprises:
configuring the sensor combination with a piston and an actuator to cause a pressure fluctuation in the concrete mixture and generate the at least one acoustic signal;
configuring the sensor combination with a pressure transducer the set distance away from the piston to sense the at least one acoustic signal and to provide associated signaling containing information about the arrival of the at least one acoustic wave; and
receiving, with the signal processor, the associated signaling and determining with the signal processor a speed of sound (SOS) in the concrete mixture and the GVF of the concrete mixture, including by using a Wood's equation based on a SOS measurement.

32. A method according to claim 17, wherein the stiffness of the concrete mixture includes, or takes the form of, the rigidity of the concrete mixture as an object, including the extent to which the concrete mixture resists deformation in response to an applied force.

33. A method according to claim 17, wherein the method comprises: configuring the signal processor and at least one memory including computer program code to implement steps for the receiving in the signal processor signaling containing information about the stiffness and the gas volume fraction (GVF) of the concrete mixture; and determining, in the signal processor, the corresponding signaling containing information about the average bubble size of gas contained in the concrete mixture, based at least partly on the signaling received.

34. Apparatus comprising:
a sensor combination configured to: sense a force imparted on a concrete mixture and a response to the force imparted, and provide signaling containing information about a stiffness and a gas void fraction (GVF) of the concrete mixture based upon the force and the response to the forced imparted; and
a signal processor configured with at least one memory including computer program code, to cause the apparatus at least to:
receive the signaling; and
determine corresponding signaling containing an average bubble size of gas contained in the concrete mixture, based at least partly on the signaling received.

35. Apparatus according to claim 34, wherein the sensor combination comprises: a combination of a force probe connected to an acoustic piston and a displacement sensor that is configured to provide associated signaling containing information used to determine the stiffness of the concrete mixture.

36. Apparatus according to claim 34, wherein the sensor combination comprises: a combination configured with a piston to impart the force into the concrete mixture, a drive current sensor to sense a drive current sent to the piston, and a piston accelerometer to sense an acceleration of the piston's motion, and also configured to provide associated signaling containing information used to determine the stiffness of the concrete mixture.

37. Apparatus according to claim 34, wherein the sensor combination comprises: a combination configured with a piston to apply an impulsive force to the concrete mixture and at least one sensor to sense or determine a displacement of the piston when the impulsive force is applied to the concrete mixture, the impulsive force applied to the concrete mixture and subsequent dampening of the piston's motion, and also configured to provide associated signaling containing information used to determine the stiffness of the concrete mixture.

38. Apparatus according to claim 34, wherein the sensor combination comprises: a pressure transducer configured to sense at least one acoustic signal injected into the concrete mixture and provide associated signaling containing information about the at least one acoustic signal sensed.

39. Apparatus according to claim 38, wherein the signal processor is configured to receive the associated signaling and to determine the GVF of the concrete mixture, based at least partly on the associated signaling.

* * * * *